United States Patent
Yamaguchi et al.

(10) Patent No.: US 7,071,352 B2
(45) Date of Patent: Jul. 4, 2006

(54) PROCESSES FOR PREPARATION OF 2-ALKYL-2-ADAMANTYL ESTERS

(75) Inventors: Masao Yamaguchi, Yamaguchi (JP); Yoshihiro Hirota, Yamaguchi (JP); Hiromasa Yamamoto, Yamaguchi (JP)

(73) Assignee: Tokuyama Corporation, Tokuyama (JP)

( * ) Notice: Subject to any disclaimer, the term of this patent is extended or adjusted under 35 U.S.C. 154(b) by 543 days.

(21) Appl. No.: 10/333,733

(22) PCT Filed: Jul. 18, 2001

(86) PCT No.: PCT/JP01/06208

§ 371 (c)(1),
(2), (4) Date: Jan. 27, 2003

(87) PCT Pub. No.: WO02/10112

PCT Pub. Date: Feb. 7, 2002

(65) Prior Publication Data

US 2003/0158437 A1 Aug. 21, 2003

(30) Foreign Application Priority Data

| Jul. 27, 2000 | (JP) | ................................ 2000-227158 |
| Aug. 10, 2000 | (JP) | ................................ 2000-242158 |
| Dec. 22, 2000 | (JP) | ................................ 2000-390533 |

(51) Int. Cl.
*C07L 69/52* (2006.01)

(52) U.S. Cl. .................................... 560/220
(58) Field of Classification Search ............... 560/220
See application file for complete search history.

(56) References Cited

FOREIGN PATENT DOCUMENTS

| JP | 5-43511 | 2/1993 |
| JP | 6-122652 | 5/1994 |
| JP | 10-182552 | 7/1998 |
| JP | 2000-229911 | 8/2000 |
| JP | 2000-309558 | 11/2000 |

OTHER PUBLICATIONS

Patent Abstracts of Japan, JP 10–182552, Jul. 7, 1998.
Patent Abstracts of Japan, JP 06–122652, May 6, 1994.
Patent Abstracts of Japan, JP 05–043511, Feb. 23, 1993.
Patent Abstracts of Japan, JP 2000–229911, Aug. 22, 2000.
Patent Abstracts of Japan, JP 2000–309558, Nov. 7, 2000.

*Primary Examiner*—Paul J. Killos
(74) *Attorney, Agent, or Firm*—Oblon, Spivak, McClelland, Maier & Neustadt, P.C.

(57) ABSTRACT

A magnesium halide salt of a 2-alkyl-2-adamantanol is reacted with a carboxylic acid halide such as acrylic chloride or the like in the presence of a tertiary amine to produce a 2-alkyl-2-adamantyl ester (the first invention).

A 2-alkyl-2-adamantanol is reacted with a carboxylic acid such as acrylic acid or the like in the presence of an acid catalyst such as concentrated sulfuric acid or the like and a drying agent composed of an acidic or neutral inorganic compound (e.g. magnesium sulfate) which is a solid at ordinary temperature in a dried state or of a water-absorbing high-molecular compound, to produce a 2-alkyl-2-admantyl ester (the second invention).

The above ester is important as a raw material for a resist for semiconductor production.

7 Claims, No Drawings

PROCESSES FOR PREPARATION OF 2-ALKYL-2-ADAMANTYL ESTERS

TECHNICAL FIELD

The present invention relates to a process for producing a 2-alkyl-2-adamntyl ester which is useful as, for example, a raw material for semiconductor resist.

BACKGROUND ART

It is reported in, for example, JP-A-5-265212 that resists produced by using a 2-alkyl-2-adamantyl ester as a raw material shows high resistance to dry etching in a process for production of semiconductor. Therefore, attention is being paid to a future prospect of 2-alkyl-2-adamantyl ester as a raw material for semiconductor resist.

For production of 2-alkyl-2-adamantyl ester, there are known, for example, a process which comprises subjecting 2-adamantanone to alkylation using an alkylation reagent composed of an organometallic compound and then subjecting the resulting metal salt of 2-alkyl-2-adamantanol to acylation using a carboxylic acid halide compound. Specifically, it is described in JP-A-10-182552 that 2-methyl-2-adamantyl methacrylate is obtained at a yield of 85.0% by using 2-adamantanone, methyl magnesium bromide and methacrylic chloride.

In such a production process, conditions are known in which an alkylation reaction of 2-admantanone using methyl magnesium bromide proceeds stoichiometrically. Therefore, the yield of the latter step, i.e. the acylation reaction of magnesium halide salt of adamantanol has an influence on the yield and purity of intended product, i.e. 2-alkyl-2-adamantyl ester.

The present inventors traced the acylation reaction described in the above literature; however, the reaction was not complete even when the reaction was made at room temperature for 15 hours, the conversion was 86%, and the purity of the intended product obtained was 77%.

When the 2-alkyl-2-adamantyl ester is used as a raw material for semiconductor resist, the ester is required to have a high purity. In the conventional production process therefor, however, the conversion in acylation is low as mentioned above and complicated purification is necessary, making it impossible to produce a 2-alkyl-2-adamantyl ester of high purity efficiently.

Further, the carboxylic acid halide compound used in the production process is ordinarily produced from a carboxylic acid compound and therefore is more expensive than the carboxylic acid compound. Furthermore, the carboxylic acid halide compound is highly reactive per se and therefore may require care in handling.

Incidentally, as a general process for production of an ester compound, there is a process which comprises reacting an alcohol compound with a carboxylic acid compound in the presence of an acid catalyst. In this process, the reaction is conducted with removing the water as by-product by azeotropic dehydration (for example, Azeotropic Dehydration, Organic Synthesis 1973, Vol. V, p. 762).

The process is conducted by a simple operation and therefore is particularly useful as an industrial process for production of ester compound when the alcohol compound and carboxylic acid compound used are inexpensive.

In this process, however, dehydration reaction of alcohol takes place preferentially as shown in Comparative Example 7 described later, when a tertiary alcohol such as 2-alkyl-2-adamantanol is used as a raw material. As a result, the process has a problem in that the yield of alkyladamantyl ester is strikingly low.

DISCLOSURE OF THE INVENTION

In order to solve the above problems, the present inventors made a study on a method by which the reaction of a magnesium halide salt of a 2-alkyl-2-adamantanol with a carboxylic acid halide compound can be allowed to proceed efficiently. As a result, it was found out that the reaction of a magnesium halide salt of a 2-alkyl-2-adamantanol with a carboxylic acid halide compound proceeds quantitatively in a short time when the reaction is conducted in the presence of a tertiary amine compound. The finding has led to the completion of the first invention. Hence, the first invention aims at providing a process for producing a 2-aklyl-2-adamantyl alkyl-2-adamantyl ester of high purity efficiently.

The present inventors made a study also on utilization, in production of a 2-alkyl-2-adamantyl ester, of the above-mentioned process for production of an ester compound using azeotropic dehydration. As a result, it was found out that even when a reaction is conducted in the presence of an acid catalyst, no dehydration of 2-alkyl-2-adamantanol takes place when a particular drying agent is allowed to coexist and that a 2-alkyl-2-adamantyl ester of high purity can be produced efficiently. This finding has led to the completion of the second invention.

Hence, the second invention aims at providing a efficient process for producing a 2-alkyl-2-adamantyl ester of high purity using a 2-alkyl-2-adamantanol as a starting material without using an expensive compound such as carboxylic acid halide compound.

BEST MODE FOR CARRYING OUT THE INVENTION

The First Invention

The first invention lies in a process for producing a 2-alkyl-2-adamantyl ester, which comprises reacting a magnesium halide salt of a 2-alkyl-2-adamantanol, represented by the following general formula (1):

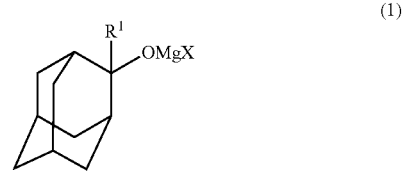

(wherein $R^1$ is an alkyl group of 1 to 6 carbon atoms, and X is a halogen atom) with a carboxylic acid halide compound in the presence of a tertiary amine compound.

The present invention is not restricted by a theory. However, in the present invention, it is presumed that the tertiary amine compound coexisting in the reaction system activates the carboxylic acid halide compound, a higher conversion is obtained thereby, and the 2-alkyl-2-adamantyl ester obtained finally has a higher purity. Moreover, it is surprising that in the activation of the carboxylic acid halide compound, the tertiary amine compound acts like a catalyst. That is, the carboxylic acid halide compound is activated sufficiently even when the tertiary amine compound is used in an amount of less than 1 mole (less than the stoichiometric amount) relative to 1 mole of the carboxylic acid halide compound. For example, when in a reaction of esterifying a magnesium halide salt of a 2-alkyl-2-adamantanol, of the general formula (1) wherein $R^1$ is an alkyl group of 1 to 3 carbon atoms, a tertiary amine compound of 0.01 to 0.5 mole per 1 mole of a carboxylic acid halide compound is allowed to coexist, a 2-alkyl-2-adamantyl ester can be obtained at a conversion of about 95% in a short time.

When in the reaction, the carboxylic acid halide compound is used in excess relative to the magnesium halide salt of a 2-alkyl-2-adamantanol, the resulting 2-alkyl-2-adamantyl ester may be decomposed by, for example, the excess carboxylic acid halide or an acid which is a thermal decomposition product thereof. In the production process of the present invention, however, such decomposition is thought to be prevented by capturing of the acid or the like by the tertiary amine compound. This decomposition is effectively prevented even when the molar ratio of the carboxylic acid halide to the magnesium halide salt was changed in a wide range.

In the production process of the present invention, a magnesium halide salt of a 2-alkyl-2-adamantanol, represented by the general formula (1) is mixed and reacted with a carboxylic acid halide compound in the presence of a tertiary amine compound to give rise to acylation to produce a 2-alkyl-2-adamantyl ester of corresponding structure.

In the above general formula (1), $R^1$ is an alkyl group of 1 to 6 carbon atoms, and X is a halogen atom.

$R^1$ is not critical as long as it is an alkyl group of 1 to 6 carbon atoms. $R^1$ is preferably an alkyl group of 1 to 3 carbon atoms, such as methyl group, ethyl group, propyl group, isopropyl group or the like in view of high utility as a raw material for a resist for semiconductor production.

As the halogen atom shown by X, there can be mentioned a fluorine atom, a chlorine atom, a bromine atom and an iodine atom. X is preferably a chlorine atom or a bromine atom in view of the good availability of raw material and most preferably a bromine atom in view of the high reactivity.

The magnesium halide salt of a 2-alkyl-2-adamantanol, represented by the general formula (1), which can be preferably used in the present invention, can be exemplified by magnesium chloride salt of 2-methyl-2adamantanol, magnesium bromide salt of 2-methyl-2-adamantanol, magnesium chloride salt of 2-ethyl-2-adamantanol, and magnesium bromide salt of 2-ethyl-2-adamantanol. Of these, preferred is a magnesium halide salt of a 2-alkyl-2-adamantanol, of the general formula (1) wherein $R^1$ is an alkyl group of 1 to 3 carbon atoms, from the high reactivity, and particularly preferred is magnesium bromide salt of 2-methyl-2-adamantanol.

The compound represented by the general formula (1) can be produced easily from 2-adamantanone and a Grignard reagent. The reaction product can be used as it is. Or, it is as necessary purified by filtration, washing or the like and is used.

The carboxylic acid halide compound is not critical as long as it is a halide compound of a carboxyl group-containing organic acid. As specific examples of the carboxylic acid halide compound used in the present invention, there can be mentioned saturated carboxylic acid halide compounds such as acetic fluoride, acetic chloride, acetic bromide, acetic iodide, propionic chloride, propionic bromide, propionic iodide and the like; unsaturated carboxylic acid halide compounds such as acrylic fluoride, acrylic chloride, acrylic bromide, acrylic iodide, methacrylic fluoride, methacrylic chloride, methacrylic bromide, methacrylic iodide and the like; and aromatic carboxylic acid halide compounds such as benzoyl fluoride, benzoyl chloride, benzoyl bromide, benzoyl iodide, toluyl fluoride, toluyl chloride, toluyl bromide, toluyl iodide, naphthoic fluoride, naphthoic chloride, naphthoic bromide and the like.

Of these, preferred are carboxylic acid chlorides of 2 to 7 carbon atoms for the high reactivity, and particularly preferred are acrylic chloride and methacrylic chloride for the high utility as a raw material for semiconductor resist.

As such carboxylic acid halide compounds, there can be used those which are available as a reagent or as an industrial material, as they are, or those obtained by subjecting such a reagent or industrial material as necessary to purification such as recrystallization, distillation or the like. Carboxylic acid halide compounds of low availability can be synthesized as follows. That is, a carboxylic acid fluoride, a carboxylic acid chloride, a carboxylic acid bromide and a carboxylic acid iodide can be easily synthesized respectively by reacting cyanuric fluoride, thionyl chloride, dibromotriphenylphosphorane and sodium iodide with a corresponding carboxylic acid or carboxylic acid chloride.

The amount of the carboxylic acid halide compound used is not critical but is preferably 0.8 to 2.0 moles per 1 mole of the used magnesium halide salt of a 2-alkyl-2-adamantanol, more preferably 1 to 1.5 moles. When the amount is less than 0.8 mole, unreacted magnesium halide salt of a 2-alkyl-2-adamantanol remains in the reaction product, reducing the purity of the reaction product. When the amount is more than 2.0 moles, an operation such as alkali treatment or the like is required for removal of unreacted carboxylic acid halide compound in the reaction product, making the operation complicated.

In reacting the magnesium halide salt of a 2-alkyl-2-adamantanol with the carboxylic acid halide compound, a tertiary amine compound is allowed to coexist. When the reaction is conducted in the absence of a tertiary amine compound, the conversion is low and no intended object is attainable.

The tertiary amine compound used in the present invention can be exemplified by aliphatic tertiary amine compounds such as trimethylamine, triethylamine, tripropylamine, tributylamine, diisopropylmethylamine, diisopropylethylamine and the like; cyclic tertiary amine compounds such as N-methylpyrrolidine, N-methylpiperidine, N-ethylpiperidine, N-methylmorpholine, N-ethylmorpholine and the like; cyclic unsaturated hydrocarbon tertiary amine compounds such as pyridine, N,N-dimethylaminopyridine and the like; and aliphatic tertiary diamine compounds such as N,N,N',N'-tetramethylethylenediamine, N,N,N',N'-tetraethylethylenediamine and the like. Of these, particularly preferred are triethylamine and N-methylmorpholine for the industrial availability and low cost. Incidentally, these tertiary amine compounds are each available as a reagent and an industrial material.

The amount of the tertiary amine compound used is not critical but a sufficient effect is obtained in an amount of 0.01 to 1.0 mole per 1 mole of the carboxylic acid halide compound. The amount is preferably 0.01 to 0.5 mole, particularly preferably 0.1 to 0.3 mole per 1 mole of the carboxylic acid halide compound in order to avoid excessive use, increase the rate of reaction and prevent the side reaction.

The reaction of the magnesium halide salt of a 2-alkyl-2-adamantanol with the carboxylic acid halide compound in the presence of the tertiary amine compound is not critical and can be conducted by mixing these raw materials for reaction appropriately. The reaction is preferably conducted in a solvent in view of, for example, the operability and the easiness of control of reaction conditions such as reaction temperature and the like. Particularly preferably, the reaction is conducted by dissolving or suspending a magnesium halide salt of a 2-alkyl-2-adamantanol and a tertiary amine compound in a solvent, adding thereto a carboxylic acid halide compound, and stirring the mixture.

The solvent used is not critical as long as it is stable to the magnesium halide salt of a 2-alkyl-2-adamantanol, the carboxylic acid halide compound and the tertiary amine compound. The solvent is preferably a hydrocarbon such as benzene, toluene or the like, or an ether such as diethyl ether, diisopropyl ether, tetrahydrofuran, 1,4-dioxane or the like, in view of the solubility of the above compounds, the rate of reaction, etc.

These organic solvents can be used singly or in admixture of two or more kinds. The amount of the organic solvent used is not critical but is preferably 5 liters or less, particularly preferably 0.2 to 3 liters per mole of the magnesium halide salt. of a 2-alkyl-2-adamantanol in view of reactor yield, solubility and rate of reaction.

The reaction conditions used in the production process of the present invention are controlled depending upon, for example, the kinds, amounts and concentrations of the used raw materials for reaction, while the proceeding of reaction is confirmed by, for example, gas chromatography. Since the reaction is conducted at a high rate with the side reaction being suppressed, it is generally preferred that the reaction temperature is 0 to 5° C. and the reaction time is 0.5 to 24 hours. Since this reaction is exothermic, it is preferred to conduct stirring during the reaction in order to make uniform the liquid temperature of reaction system.

By thus conducting the reaction, it is possible to obtain a 2-alkyl-2-adamantyl ester having a molecular structure corresponding to the molecular structures of the materials used. For example, when magnesium bromide salt of 2-methyl-2adamantanol is used as the magnesium halide salt of a 2-alkyl-2-adamantanol and methacrylic chloride is used as the carboxylic acid halide compound, 2-methyl-2-adamantyl methacrylate is formed.

The isolation of a 2-alkyl-2-adamantyl ester from the reaction mixture is conducted by an ordinary method. For example, first, the reaction mixture is washed with an aqueous acid solution to remove a magnesium halide from the reaction mixture; then, further washing with an aqueous alkali solution, water, etc. is conducted; the resulting organic layer is subjected to vacuum evaporation to remove the solvent contained therein; thereby, a 2-alkyl-2-adamantyl ester is isolated.

According to the present production process, a 2-alkyl-2-adamantyl ester is formed nearly quantitatively; therefore, even when isolation is conducted by such a simple method, the resulting product has a high purity. Therefore, the reaction mixture can be used per se without purification, depending upon the application thereof. When a product of higher purity is needed, the resulting 2-alkyl-2-adamantyl ester is purified by column chromatography, distillation, recrystallization or the like, depending upon the properties of the ester.

According to the first invention of the present invention, a 2-alkyl-2-adamantyl ester of high purity can be obtained from a magnesium halide salt of a 2-alkyl-2-adamantanol and a carboxylic acid halide compound, in short time at a high yield in a simple operation.

The Second Invention

The second invention lies in a process for producing a 2-alkyl-2-adamantyl ester, which comprises reacting a 2-alkyl-2-admantanol with a carboxylic acid compound in the presence of an acid catalyst and a drying agent composed of an acidic or neutral inorganic compound which is a solid at ordinary temperature in a dried state or water-absorbing high-molecular compound.

According to the production process of the present invention, a 2-alkyl-2-adamantyl ester can be obtained at a higher yield than when an ordinary process using azeotropic dehydration is used. The drying agent used in the reaction of the present process can be separated from the reaction mixture after the reaction, by a simple operation such as filtration or the like. The drying agent separated from the reaction mixture can generally be reutilized by regeneration. Moreover, since no carboxylic halide compound is used as a reactant, the reaction can be conducted simply as mentioned previously with no necessity of worrying about the cost and chemical instability of the compound.

When there is used, as the acid catalyst, a cationic ion exchange resin having sulfonic acid group as the ion exchange group (this resin is hereinafter referred to simply as cationic ion exchange resin), the cationic ion exchange resin can be separated from the reaction mixture after the reaction, together with the drying agent, by a simple operation such as filtration or the like; therefore, a 2-alkyl-2-adamantyl ester of high purity can be obtained by a simple post-treatment.

The 2-alkyl-2-adamantanol which is a starting material of the present production process, has a structure in which an alkyl group and a hydroxyl group are bonded to the 2-position carbon atom of adamantane molecule. The kind of the alkyl group of the 2-alkyl-2-adamantanol is not critical and any known compound can be used.

A 2-alkyl-2-adamantanol having a straight or branched chain alkyl group of 1 to 4 carbon atoms is important as a starting material of the present invention in view of the high utility as a raw material for semiconductor resist.

As specific examples of the 2-alkyl-2-adamantanol, there can be mentioned 2-methyl-2-adamantanol, 2-ethyl-2-adamantanol, 2-propyl-2-adamantanol, 2-isopropyl-2-adamantanol and 2-butyl-2-adamantanol.

Of these, 2-methyl-2-adamantanol or 2-ethyl-2-adamantanol is particularly important for the high utility for resist production. 2-Methyl-2-adamantanol is most preferred as a starting material in view of the high reactivity.

As the 2-alkyl-2-adamantanol, those marketed commercially or those produced using 2-adamantanone and an organometallic reagent can be used as they are or after being purified as necessary by a method such as recrystallization, sublimation or the like.

As to the carboxylic acid compound used as another raw material, there is no particular restriction as long as it an organic compound having carboxyl group. As specific examples of the carboxylic acid compound used in the present invention, there can be mentioned saturated monocarboxylic acid compounds such as formic acid, acetic acid, propionic acid and the like; saturated dicarboxylic acid compounds such as oxalic acid, malonic acid, succinic acid and the like; unsaturated carboxylic acid compounds such as acrylic acid, methacrylic acid, propiolic acid, crotonic acid, maleic acid and the like; and carbon ring or heterocyclic ring carboxylic acid compounds such as benzoic acid, 1-naphthoic acid, phthalic acid, nicotinic acid, 2-furancarboxylic acid and the like.

Of these, carboxylic acid compounds of 2 to 7 carbon atoms are preferred for the high reactivity. Acrylic acid or methacrylic acid is particularly preferred for the high utility as a raw material for semiconductor resist. As to these carboxylic acid compounds as well, those marketed commercially can be used as they are or after being purified as necessary by a method such as recrystallization, distillation or the like.

The carboxylic acid compound reacts with the 2-alkyl-2-adamantanol nearly stoichiometrically and therefore is used in an amount of about 1 mole per 1 mole of the 2-alkyl-2-adamantanol. However, it is preferred that either of them is used in an excess for a higher reaction rate. Since the carboxylic acid compound is less expensive than the 2-alkyl-2-adamantanol, the carboxylic acid compound is ordinarily used in an amount of preferably 1 to 50 moles, more preferably 2 to 20 moles per 1 mole of the 2-alkyl-2-adamantanol.

The acid catalyst used in the present invention is not critical as long as it is an acid having an catalytic activity for enhancing the rate of esterification reaction between the 2-alkyl-2-adamantanol and the carboxylic acid compound, and any of such acids can be used. Specifically there can be used, as the acid catalyst, organic acids and inorganic acids which are generally used as a catalyst in an esterification reaction conducted using, as raw materials, an alcohol compound and a carboxylic acid compound.

Incidentally, when the acid catalyst is used also as a drying agent described later, it is not necessary to add other drying agent to the acid catalyst and the acid catalyst may be allowed to have a function of a drying agent.

The acid catalyst is preferably a strong acid having an acid dissociation constant pKa of 3 or less, in view of the level of the catalytic activity. As preferred examples of the acid catalyst, there can be mentioned inorganic acid compounds such as sulfuric acid, phosphoric acid and the like, and organic acid compounds such as toluenesulfonic acid, trifluoroacetic acid and the like.

The amount of the acid catalyst used is not critical but is preferably 0.001 to 1 part by mass, particularly preferably 0.01 to 0.1 part by mass per part by mass of the 2-alkyl-2-adamantanol. By using the acid catalyst in an amount of the above range, a higher reaction rate is obtained and a side reaction can be prevented.

Further, in the present invention, there can also be used preferably, as the acid catalyst, a cationic ion exchange resin having sulfonic acid group as the ion exchange group. The cationic ion exchange resin is not critical as long as it has sulfonic acid group as the ion exchange group.

In general, ion exchange resins take a gel type or a porous type [e.g. a macroreticular (MR) type (referred to also as a high porous type)]. An ion exchange resin of any type can be used. However, use of a MR type is preferred in view of the resin stability during reaction and the high reactivity. Incidentally, as to the sulfonic acid group as ion exchange group, there are a sulfonic acid ($-SO_3H$) type and a sulfonic acid salt (an alkali metal salt such as $-SO_3Na$) type. In the present invention, use of a sulfonic acid ($-SO_3H$) type is necessary because the ion exchange resin is allowed to act as an acid catalyst. A sulfonic acid salt (an alkali metal salt such as $-SO_3Na$) type per se does not function as an acid catalyst. However, it can function as an acid catalyst by converting it into a sulfonic acid ($-SO_3H$) type by a known pretreatment of ion exchange group such as hydrochloric acid treatment, sulfuric acid treatment or the like. Such cationic ion exchange resins are marketed and available commercially.

When a cation exchange resin is used as the acid catalyst, ordinarily its amount used is preferably 0.001 to 100 parts by mass, particularly preferably 0.01 to 50 parts by mass per part by mass of the 2-alkyl-2-adamantanol in view of the rate of reaction and the easiness of stirring. Preferably, the amount used is specifically controlled depending upon the kind of the cation exchange resin used, by confirming the proceeding of the reaction by, for example, gas chromatography.

In the production process of the present invention, when a 2-alkyl-2-adamantanol is reacted with a carboxylic acid compound using an acid catalyst, to obtain an ester, it is essential to conduct the reaction in the presence of a particular drying agent.

The drying agent used in the present invention is an acidic or neutral inorganic compound which is a solid in a dried state at normal temperature or water-absorbing high-molecular compound. With a drying agent which is a liquid when dried, or with a basic drying agent, the advantage of the present invention is unobtainable.

The drying agent is not critical as long as it can absorb the water present in the solution and per se is acidic or neutral.

Incidentally, in the present invention, the solid material refers to a solid or a gel. Further, the drying agent referred to in the present invention includes a dehydrating agent.

The inorganic compound which is a solid at ordinary temperature in a dried state, can be exemplified by magnesium sulfate, calcium sulfate, phosphorus pentoxide, a molecular sieve and a silica gel.

The water-absorbing high-molecular compound which is a solid material at ordinary temperature in a dried state, can be exemplified by a cationic ion exchange resin and a polyacrylamide gel.

These drying agents may be used singly or in combination of two or more kinds.

The amount of the drying agent used is not critical as long as it is sufficient to absorb the water generated in the reaction. Ordinarily, it is determined appropriately depending upon the amounts of 2-alkyl-2-adamantanol and carboxylic acid compound used and the kind of drying agent used. It is preferred to be ordinarily 0.1 to 100 parts by mass, particularly 0.2 to 50 parts by mass per part by mass of the 2-alkyl-2-adamantanol.

By conducting esterification in the presence of such a drying agent, the production of an olefin compound (a by-product) brought about by the dehydration of 2-alkyl-2-adamantanol is prevented effectively and an intended ester compound can be obtained at a high yield.

The reaction of the 2-alkyl-2-adamantanol with the carboxylic acid compound in the presence of the acid catalyst and the drying agent is not critical and can be conducted by mixing these materials appropriately. From the standpoints of the operability and the easiness of control of reaction conditions such as reaction temperature and the like, it is preferred to dissolve or suspend a 2-alkyl-2-adamantanol and a carboxylic acid compound in a solvent, add thereto an acid catalyst and a drying agent, and stirring them.

The solvent used is not critical as long as it is stable to acids. Preferred solvents are, for example, hydrocarbons such as hexane, toluene and the like, and chlorinated hydrocarbons such as methylene chloride, chloroform and the like from the standpoint of, for example, the solubility of compounds. The amount of the solvent used is not critical. In view of the solubilities of starting material compounds and product compound, the reactor yield, etc., the amount is preferably 5 liters or less, particularly preferably 2 to 1 liter per mole of the alkyladamantanol.

The reaction conditions are determined appropriately depending upon the kinds, amounts and concentrations of the individual starting materials used. The reaction temperature is preferably 0 to 40° C., and the reaction time is preferably 1 to 48 hours. By selecting these reaction conditions, it is possible to conduct a reaction at a high reaction rate with a side reaction being prevented. The proceeding of the reaction can be confirmed by, for example, gas chromatography.

By thus conducting an esterification reaction, there can be obtained a 2-alkyl-2-adamantyl ester having a structure obtained by dehydration and condensation between a 2-alkyl-2-adamantanol and a carboxylic acid compound.

For example, by conducting a reaction using, as the 2-alkyl-2-adamantanol, 2-methyl-2-adamantanol and, as the carboxylic acid compound, acrylic acid or methacrylic acid, there is obtained 2-methyl-2-adamantyl acrylate or 2-methyl-2-adamantyl methacrylate.

To recover an intended compound of 2-alkyl-2-adamantyl ester from the reaction mixture after esterification, the following method can be shown, for example. First, the drying agent is removed from the reaction mixture by filtration or the like; then, the drying agent-removed reaction mixture is washed with an aqueous alkali solution to neutralize the acid catalyst in the reaction mixture. Further, water washing and extraction are conducted as necessary; the resulting mixture is subjected to vacuum evaporation to remove the solvent contained therein. Thereby, an intended ester compound can be isolated.

When the reaction is conducted using a cationic ion exchange resin as an acid catalyst, the acid catalyst and the drying agent can be removed by removing the cationic ion exchange resin and drying agent used, by filtration or the like. Therefore, by subjecting the resulting mixture to vacuum evaporation to remove the solvent contained therein, without conducting water washing and extraction, an intended ester compound can be isolated.

When the reaction is conducted using a cationic ion exchange resin as an acid catalyst and drying agent, the acid catalyst and drying agent can be removed by removing, from the reaction mixture, the cationic ion exchange resin used, by filtration or the like. Therefore, by subjecting the reaction mixture to vacuum evaporation to remove the solvent contained therein, without conducting water washing and extraction, an intended ester compound can be isolated.

The cationic ion exchange resin and the drying agent both removed by filtration or the like can be regenerated by a known regeneration treatment such as heat treatment, vacuum drying or the like and can be reutilized.

In the production process of the present invention, a side reaction is suppressed sufficiently and a main reaction proceeds selectively at a high conversion. Therefore, an intended compound of high purity can be obtained by a simple isolation method such as mentioned above. As a result, it can be used per se in various applications without conducting further purification, depending on the application. When an intended compound of higher purity is needed, the isolated 2-alkyl-2-adamantyl ester can be subjected to further purification by a known method such as column chromatography, distillation, recrystallization or the like, depending upon the properties of the ester.

According to the present invention, a side reaction is suppressed and a main reaction proceeds selectively at a high conversion; therefore, a 2-alkyl-2-adamantyl ester of high purity can be obtained by a simple operation. Further, since no unstable acid halide compound is used, the reaction operation is simple.

EXAMPLES

The present invention is specifically described below by way of Examples. However, the present invention is in no way restricted by these Examples.

Examples of the First Invention

Example 1

44 ml of a tetrahydrofuran solution containing 0.06 mole of methyl magnesium bromide was added into a 200-ml four-necked flask provided with a stirrer and a drying tube filled with calcium chloride. The air in the flask was replaced by nitrogen. Then, into the flask was dropwise added 7.5 g (0.05 mole) of 2-adamantanone dissolved in 30 ml of tetrahydrofuran, with the temperature of the mixture in the flask being controlled so as not to exceed 40° C. After the completion of the dropwise addition, the mixture in the flask was stirred at 50° C. for 3 hours.

The reaction mixture was analyzed by gas chromatography (GC). As a result, magnesium bromide salt of 2-methyl-2-adamantanol was formed by nearly 100%.

The reaction mixture (a tetrahydrofuran solution of magnesium bromide salt of 2-methyl-2-adamantanol) was cooled to room temperature. Thereto was added 1.62 g (0.016 mole) of triethylamine. Then, into the flask was dropwise added 6.90 g (0.066 mole) of methacrylic chloride in a nitrogen atmosphere with the temperature of the mixture in the flask being controlled at 25° C. Stirring was continued at 25° C. after the completion of the dropwise addition. The proceeding of a reaction was traced by GC. As a result, the reaction was almost complete in 3 hours. The conversion based on magnesium bromide salt of 2-methyl-2-adamantanol, determined by GC was 95.5%.

To the reaction mixture was added 1.25 ml of deionized water to stop the reaction. 0.02 g of phenothiazine as a polymerization inhibitor was added to the reaction mixture. Then, vacuum evaporation was conducted to remove the solvent to obtain a distillation residue. 75 g of heptane was added to the residue. The heptane layer was washed with an aqueous solution containing 1 mole/liter of ammonium chloride. The heptane layer was further washed with an aqueous solution containing 10% of sodium hydroxide and deionized water in this order. Then, heptane was removed by vacuum evaporation to obtain 11.6 g of a crude product of 2-methyl-2-adamantyl methacrylate (0.048 mole, yield: 99.1% in terms of magnesium bromide salt of 2-methyl-2-adamantanol). This crude product of 2-methyl-2-adamantyl methacrylate was analyzed by GC. As a result, the purity based on GC peak area (this purity is hereinafter referred to also as GC purity) was 93.1%.

Incidentally, GC purity 93.1% is high as the purity of 2-methyl-2-adamantyl methacrylate; and this crude product can be used per se as a product without conducting further purification, depending upon the application.

Examples 2 to 7

An operation was conducted in the same manner as in Example 1 except that the temperature of methacrylic chloride addition and the temperature of reaction were changed as shown in Table 1. The results obtained are shown in Table 1. In Table 1, the conversion refers to a conversion based on magnesium bromide salt of 2-methyl-2-adamantanol, determined by GC analysis. The yield is a yield of a crude product of 2-methyl-2-asamantyl methacrylate. The purity is a purity based on the peak area of GC (the same applies in the following Tables regarding the first invention).

TABLE 1

| Example | Addition temperature of methacrylic chloride ° C. | Reaction temperature ° C. | Reaction time hr | Conversion % | Yield % | Purity % |
|---|---|---|---|---|---|---|
| 2 | 0 | 50 | 1.5 | 96.6 | 99.4 | 89.3 |
| 3 | −20 | 50 | 1.5 | 95.5 | 99.3 | 90.1 |
| 4 | 25 | 25 | 15.0 | 98.1 | 99.1 | 95.3 |
| 5 | 25 | 50 | 3.0 | 97.4 | 99.2 | 91.7 |
| 6 | 40 | 50 | 3.0 | 96.0 | 99.2 | 89.3 |
| 7 | 50 | 50 | 3.0 | 92.2 | 99.5 | 85.8 |

Examples 8 to 9

An operation was conducted in the same manner as in Example 1 except that a tertiary amine shown in Table 2 was used. The results obtained are shown in Table 2.

TABLE 2

| Example | Tertiary amine compound | Conversion % | Yield % | Purity % |
|---|---|---|---|---|
| 8 | N-methylmorpholine | 95.8 | 99.6 | 91.5 |
| 9 | Diisopropylethylamine | 94.5 | 98.9 | 98.1 |

Examples 10 to 11

An operation was conducted in the same manner as in Example 1 except that a solvent shown in Table 3 was used. The results obtained are shown in Table 3.

TABLE 3

| Example | Solvent | Conversion % | Yield % | Purity % |
|---|---|---|---|---|
| 10 | Toluene | 94.6 | 99.0 | 91.6 |
| 11 | Diethyl ether | 97.5 | 99.6 | 94.3 |

Examples 12 to 14

An operation was conducted in the same manner as in Example 1 except that a carboxylic acid halide compound shown in Table 4 was used. The results obtained are shown in Table 4.

TABLE 4

| Example | Carboxylic acid halide compound | Product | Conversion % | Yield % | Purity % |
|---|---|---|---|---|---|
| 12 | Acetyl chloride | 2-Methyl-2-adamantyl acetate | 98.3 | 98.9 | 97.3 |
| 13 | Acetyl bromide | 2-Methyl-2-adamantyl acetate | 90.5 | 99.3 | 89.8 |
| 14 | Benzoyl bromide | 2-Methyl-2-adamantyl benzoate | 84.6 | 96.3 | 82.3 |

Example 15

28.6 g (1.18 moles, 1.1 times moles of 2-adamantanone) of magnesium and 950 ml of tetrahydrofuran were added into a 3-liter four-necked flask provided with a stirrer and a drying tube filed with calcium chloride, followed by stirring. The flask inside atmosphere was converted into nitrogen. Into the flask was dropwise added, at room temperature, 112 g of methyl bromide (1.18 moles, 1.1 times moles of 2-adamantanone) with the temperature of the mixture in the flask being controlled at 30° C. or less. After the completion of the addition, stirring was conducted at 25° C. for 3 hours to synthesize methyl magnesium bromide.

Next, into the flask was dropwise added a solution of 160 g (1.07 moles) of 2-adamantanone dissolved in 460 ml of tetrahydrofuran, with the temperature of the mixture in the flask being controlled so as not to exceed 50° C. After the completion of the dropwise addition, the mixture was stirred at 50° C. for 3 hours.

The proceeding of a reaction was confirmed by GC. As a result, magnesium bromide salt of 2-methyl-2-admantanol was formed by nearly 100%.

The resulting tetrahydrofuran solution of magnesium bromide salt of 2-methyl-2-admantanol was cooled to room temperature. Thereto was added 27.1 g (0.27 mole) of triethylamine, and the mixture was heated to 40° C. Then, into the flask was dropwise added, in a nitrogen atmosphere, 139.9 g (1.34 mole) of methacrylic chloride with the temperature of the mixture in the flask being controlled so as not to exceed 45° C. After the completion of the dropwise addition, stirring was conducted at 50° C. The proceeding of a reaction was traced by GC. As a result, the reaction was nearly complete in 3 hours.

The conversion based on magnesium bromide salt of 2-methyl-2-adamantanol, determined by GC analysis was 97.4%.

25 ml of deionized water was added to the reaction mixture obtained, to stop the reaction. Then, 0.5 g of phenothiazine as a polymerization inhibitor was added and vacuum evaporation was conducted for solvent removal. To the residue was added 750 g of heptane. The heptane layer was washed with an aqueous solution containing 1 mole/liter of ammonium chloride. The heptane layer was further washed with a 10% aqueous sodium hydroxide solution and deionized water, and heptane was removed by vacuum evaporation to obtain 247.8 g of a crude product of 2-methyl-2-adamantyl methacrylate (1.05 moles, yield: 94.9% based on magnesium bromide salt of 2-methyl-2-adamantanol). The GC purity of this crude product of 2-methyl-2-adamantyl methacrylate was 90.7%.

Of the crude product of 2-methyl-2-adamantyl methacrylate, 50.2 g was subjected to vacuum distillation at a vacuum of 0.3 mmHg to collect a fraction having a GC purity of 98% or more. As a result, there could be obtained 2-methyl-2-adamantyl methacrylate of GC purity of 98.4% in an amount of 38.0 g (0.16 mole, yield: 74.9% in terms of magnesium bromide salt of 2-methyl-2-adamantanol).

Comparative Example 1

44 ml of a tetrahydrofuran solution containing 0.06 mole of methyl magnesium bromide was added into a 200-ml four-necked flask provided with a stirrer and a drying tube filled with calcium chloride. There to was dropwise added, at room temperature in a nitrogen atmosphere, a solution of 7.5 g (0.05 mole) of 2-adamantanone dissolved in 30 ml of tetrahydrofuran, with the temperature of the mixture in the flask being controlled so as not to exceed 40° C. After the completion of the dropwise addition, the mixture was stirred at 50° C. for 3 hours. The proceeding of a reaction was confirmed by GC. As a result, magnesium bromide salt of 2-methyl-2-adamantanol was formed by nearly 100%.

The resulting tetrahydrofuran solution of magnesium bromide salt of 2-methyl-2-adamantanol was cooled to room temperature. Thereto was dropwise added, in a nitrogen atmosphere, 6.27 g (0.06 mole) of methacrylic chloride with the temperature of the mixture in the flask being controlled at 25° C. After the completion of the dropwise addition, stirring was continued at 25° C. and the proceeding of a reaction was traced by GC. As a result, the conversion based on magnesium bromide salt of 2-methyl-2-adamantanol was 69.4% in 3 hours and 86.3% in 15 hours.

1.25 ml of deionized water was added to the reaction mixture to stop the reaction. Further, 0.02 g of phenothiazine as a polymerization inhibitor was added to the reaction mixture. Vacuum evaporation was conducted to remove the solvent to obtain a residue. 75 g of heptane was added to the residue. The heptane layer was washed with an aqueous solution containing 1 mole/liter of ammonium chloride. The heptane layer was further washed with an aqueous solution containing 10% by mass of sodium hydroxide and deionized water. Then, heptane was removed by vacuum evaporation to obtain 12.2 g of a crude product of 2-methyl-2-adamantyl methacrylate (0.052 mole, yield: 104.3% in terms of magnesium bromide salt of 2-methyl-2-adamantanol). This crude product of 2-methyl-2-adamantyl methacrylate had a GC purity of 77.1%.

Comparative Example 1 is an case in which a reaction was conducted using no tertiary amine compound in Examples 1 and 4. As shown in the results of Examples 1 and 4, the conversions after 3 hours and 15 hours when a reaction was conducted in the co-existence of a tertiary amine compound, is 95.5% and 98.1%, respectively. In contrast, in Comparative Example 1, the conversion after 15 hours is as low as 86.3%. In Comparative Example 1, the purity of the crude product obtained in the same manner is low as well.

Thus, it is clear that when comparison is made in the same reaction system, a reaction in the co-existence of a tertiary amine compound gives an improved conversion and an improved purity of crude product.

Examples of the Second Invention

Example 16

830 mg (5 m mole) of 2-methyl-2-adamantanol and 4.32 g (50 m mole) of methacrylic acid were dissolved in 5 ml of methylene chloride. Thereto were added 100 mg of concentrated sulfuric acid (96% by mass) and 1.0 g of magnesium sulfate. Stirring was conducted at room temperature (about 25° C.) for 16 hours. Then, the reaction mixture was poured into 50 ml of an aqueous solution containing 10% by mass of sodium hydroxide, followed by extraction with 50 ml of ether. The resulting ether layer was subjected to evaporation to remove the solvent contained therein, to obtain 1.2 g of a crude product. The crude product was analyzed by gas chromatography. The content (purity) of 2-methyl-2-adamantyl methacrylate in the crude product was 84% based on the peak area of GC. Incidentally, this purity of 84% is high as the purity of 2-methyl-2-adamantyl methacrylate. A product of this purity can be used per se, depending upon the application, without conducting further purification. The above crude product was analyzed by liquid chromatography and gel permeation chromatography; as a result, there was substantially no impurity peak not appearing in the above gas chromatography. Therefore, the yield of 2-methyl-2-adamantyl methacrylate determined by the liquid chromatography and the gel permeation chromatography was 84% which was equal to the purity.

Example 17

A reaction, a post-treatment, etc. were conducted in the same operation as in Example 16 but using no methylene chloride. The yield of 2-methyl-2-adamantyl methacrylate was 84%.

Example 18

A reaction, a post-treatment, etc. were conducted in the same operation as in Example 1 except that 2.16 g (25 m mole) of methacrylic acid was used and the reaction was conducted at 4° C. for 6 hours. The yield of 2-methyl-2-adamantyl methacrylate was 81%.

Examples 19 to 21

A reaction, a post-treatment, etc. were conducted in the same operation as in Example 1 except that methylene chloride was replaced by a solvent shown in Table 1. The results are shown in Table 5.

TABLE 5

| Example | Solvent | Yield % |
|---------|---------------|---------|
| 19 | Heptane | 75 |
| 20 | Toluene | 74 |
| 21 | Ethyl acetate | 72 |

Example 22

A reaction, a post-treatment, etc. were conducted in the same operation as in Example 17 except that in place of using concentrated sulfuric acid and magnesium sulfate, 200 mg of phosphorus pentoxide was used as a catalyst and dehydrating agent. The yield of 2-methyl-2-adamantyl methacrylate was 69%.

Examples 23 to 25

A reaction, a post-treatment, etc. were conducted in the same operation as in Example 16 except that in place of using concentrated sulfuric acid, an acid catalyst shown in Table 6 was used in an amount shown in Table 6. The results are shown in Table 6.

TABLE 6

| Example | Acid catalyst/amount used | Yield % |
|---------|----------------------------------|---------|
| 23 | Phosphoric acid/100 mg | 74 |
| 24 | p-Toluenesulfonic acid/200 mg | 71 |
| 25 | Trifluoromethanesulfonic acid/50 mg | 74 |

Example 26

A reaction, a post-treatment, etc. were conducted in the same operation as in Example 16 except that methacrylic acid was replaced by 3.1 g (25 m mole) of benzoic acid and magnesium sulfate was replaced by 2 g of Molecular Sieve 4A. The yield of 2-methyl-2-adamantyl benzoate was 71%.

Example 27

A reaction, a post-treatment, etc. were conducted in the same operation as in Example 17 except that methacrylic acid was replaced by 3.0 g (50 m mole) of acetic acid. The yield of 2-methyl-2-adamantyl acetate was 74%.

Example 28

A reaction, a post-treatment, etc. were conducted in the same operation as in Example 17 except that methacrylic acid was replaced by 3.6 g (50 m mole) of acrylic acid. The yield of 2-methyl-2-adamantyl acrylate was 85%.

Example 29

33.2 g (0.2 mole) of 2-methyl-2-adamantanol was dissolved in 172.2 g (2.0 mole) of methacrylic acid. Thereto were added 4.0 g of concentrated sulfuric acid (96% by mass) and 40.0 g of magnesium sulfate. Stirring was conducted at room temperature (about 25° C.) for 4 hours. Then, the reaction mixture was dissolved in 141.0 g of heptane. The resulting solution was washed with an aqueous solution containing 10% by mass of sodium hydroxide and deionized water in this order.

The resulting organic layer was subjected to evaporation to remove the solvent contained therein, to obtain 42.9 g of a crude product. The crude product was analyzed by gas chromatography. As a result, the content of 2-methyl-2-adamantyl methacrylate in the crude product was 84%.

The crude product of 2-methyl-2-adamantyl methacrylate was subjected to vacuum distillation at a vacuum of 0.3 mmHg to obtain 31.7 g (yield: 68%) of 2-methyl-2-adamantyl methacrylate. This product had a purity of 97.5% when analyzed by gas chromatography.

Example 30

830 mg (5 m mole) of 2-methyl-2-adamantanol and 4.32 g (50 m mole) of methacrylic acid were dissolved in 5 ml of methylene chloride. To the solution were added 1.0 g of Amberlist-15 (a product of Organo Corporation, a macroreticular type, a sulfonic acid type) as a cationic ion exchange resin and 3.0 g of anhydrous calcium sulfate. Stirring was conducted at room temperature (about 25° C.) for 10 hours. Then, the reaction mixture was filtered to separate Amberlist-15 and anhydrous calcium sulfate. The separated Amberlist-15 and anhydrous calcium sulfate were washed with 20 ml of methylene chloride. The washings were combined with the filtrate obtained previously. The combined filtrate and washings were subjected to evaporation to remove the solvent, etc. contained therein, to obtain 1.2 g of a crude product. The crude product was analyzed by gas chromatography. As a result, the content of 2-methyl-2-adamantyl methacrylate in the crude product was 84%. The above crude product was analyzed by liquid chromatography and gel permeation chromatography; as a result, there was substantially no impurity peak which is not appearing in the above gas chromatography. Therefore, the yield of 2-methyl-2-adamantyl methacrylate determined by liquid chromatography and gel permeation chromatography was 84% which was equal to the purity.

Example 31

The Amberlist-15 and anhydrous calcium sulfate separated by filtration in Example 30 were regenerated by heating at 100° C. for 4 hours at a vacuum of 0.2 mmHg. In the same operation as in Example 30 except that 1.0 g of the regenerated Amberslist-15 and 3.0 g of the regenerated anhydrous calcium sulfate were used, and a reaction, a post-treatment, etc. were conducted. The yield of 2-methyl-2-adamantyl acrylate was 84%.

From this result, it is clear that a cationic ion exchange resin and a dehydrating agent both used in a reaction can be reutilized by an appropriate regeneration treatment.

Example 32

An operation was conducted in the same manner as in Example 30 except that no methylene chloride was used. As a result, the yield of 2-methyl-2-adamantyl methacrylate was 84%.

Example 33

A reaction, a post-treatment and an analysis were conducted in the same manner as in Example 15 except that no anhydrous calcium sulfate was used and 3.0 g of Amberslist-15 was used as an acid catalyst and dehydrating agent. As a result, the yield of 2-methyl-2-adamantyl acrylate was 74%.

Examples 34 to 35

A reaction, a post-treatment and an analysis were conducted in the same manner as in Example 30 except that in place of anhydrous calcium sulfate, a dehydrating agent shown in Table 7 was used in an amount shown in Table 7. The results are shown in Table 7.

TABLE 7

| Example | Dehydrating agent/g | Yield % |
| --- | --- | --- |
| 34 | Molecular Sieve 4A/1.0 | 73 |
| 35 | Magnesium sulfate/1.0 | 66 |

Example 36

A reaction, a post-treatment, etc. were conducted in the same operation as in Example 30 except that methacrylic acid was replaced by 3.0 g (50 m mole) of acetic acid. The yield of 2-methyl-2-adamantyl acetate was 72%.

Example 37

A reaction, a post-treatment, etc. were conducted in the same operation as in Example 30 except that methacrylic acid was replaced by 3.6 g (50 m mole) of acrylic acid. The yield of 2-methyl-2-adamantyl acrylate was 84%.

Example 38

33 g (0.2 mole) of 2-methyl-2-adamantanol and 172.2 g (2.0 mole) of methacrylic acid were dissolved in 200 ml of methylene chloride. To the solution were added 40.0 g of Amberlist-15 and 120.0 g of anhydrous calcium sulfate. Stirring was conducted at room temperature (about 25° C.) for 4 hours. Then, the reaction mixture was filtered to separate Amberlist-15 and anhydrous calcium sulfate. The separated Amberlist-15 and anhydrous calcium sulfate were washed with 200 ml of methylene chloride. The washings were combined with the filtrate obtained previously. The combined filtrate and washings were subjected to evaporation to remove methylene chloride and methacrylic acid to obtain 86.2 g of a crude product. The crude product was analyzed by gas chromatography. As a result, the content of 2-methyl-2-adamantyl methacrylate in the crude product was 84%.

Of the obtained crude product of 2-methyl-2-adamantyl methacrylate, 50.0 g was subjected to vacuum distillation at a vacuum of 0.3 mmHg to obtain 26.7 g (yield: 57%) of 2-methyl-2-adamantyl methacrylate. The purity of this product determined by gas chromatography was 97.5%.

Comparative Examples 2 to 5

A reaction, a post-treatment, etc. were conducted in the same operation as in Example 17 except that no magnesium sulfate was used and concentrated sulfuric acid (96% by mass) was used as a catalyst and dehydrating agent. The composition of each crude product obtained and the yield of 2-methyl-2-adamantyl methacrylate (intended product) are shown in Table 8.

TABLE 8

| Comparative Example | Concentrated sulfuric acid mg | Methacrylate yield % | Adamantanol % | By-products % |
|---|---|---|---|---|
| 2 | 100 | 47 | 45 | 2-Methylene-adamantane: 7 Others: 1 |
| 3 | 500 | 46 | 42 | 2-Methylene-adamantane: 7 Others: 1 |
| 4 | 1000 | 2 | 6 | Complicated mixture: 92 |
| 5 | 5000 | 0 | 0 | Complicated mixture: 100 |

Comparative Example 6

A reaction, a post-treatment, etc. were conducted in the same operation as in Example 16 except that no magnesium sulfate was used, hexane was used as a solvent, and the reaction was conducted at a refluxing temperature for 3 hours. 1.0 g of a crude product was obtained. However, the yield of 2-methyl-2-adamantyl methacrylate was 31%, the raw material adamantanol remained by 22%, and 2-methyleneadamantane was formed by 46%.

Comparative Example 7

A reaction was conducted at a refluxing temperature for 3 hours using no magnesium sulfate but using a Dean-Stark dehydrating apparatus. Toluene was used as a solvent. The other operating conditions were the same as in Example 16, and a reaction, a post-treatment, etc. were conducted. 1.0 g of a crude product was obtained. However, the purity of 2-methyl-2-adamantyl methacrylate in the crude product was 15% and 2-methyleneadamantane was formed by 80%.

The invention claimed is:

1. A process for producing a 2-alkyl-2-adamantyl ester, which comprises reacting a magnesium halide salt of a 2-alkyl-2-adamantanol, represented by the following general formula (1):

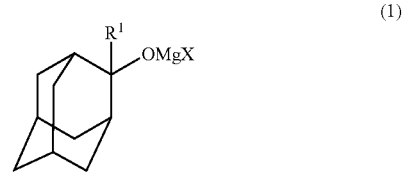

(1)

(wherein $R^1$ is an alkyl group of 1 to 6 carbon atoms, and X is a halogen atom) with a carboxylic acid halide compound in the presence of a tertiary amine compound of 0.01 to 0.5 mole per 1 mole of the carboxylic acid halide.

2. A process for producing a 2-alkyl-2-adamantyl ester according to claim 1, wherein in the general formula (1), $R^1$ is an alkyl group of 1 to 3 carbon atoms.

3. A process for producing a 2-alkyl-2-adamantyl ester according to claim 1, wherein the carboxylic acid halide is acrylic chloride or methacrylic chloride.

4. A process for producing a 2-alkyl-2-adamantyl ester according to claim 1, wherein the carboxylic acid halide is used in an amount of 0.8 to 2.0 moles per 1 mole of the magnesium halide salt of a 2-alkyl-2-adamantyl ester.

5. A process for producing a 2-alkyl-2-adamantyl ester according to claim 1, wherein the tertiary amine compound is triethylamine or N-methylmorpholine.

6. A process for producing a 2-alkyl-2-adamantyl ester according to any of claim 1, wherein the reaction is allowed to proceed in a solvent.

7. A process for producing a 2-alkyl-2-adamantyl ester according to claim 2, wherein the carboxylic acid halide is used in an amount of 0.8 to 2.0 moles per 1 mole of the magnesium halide salt of a 2-alkyl-2-adamantyl ester.

* * * * *